(12) United States Patent
Silverman et al.

(10) Patent No.: US 6,882,412 B2
(45) Date of Patent: Apr. 19, 2005

(54) METHOD FOR INSPECTING AN INTERNAL FLOATING ROOF IN A LIQUID-CONTAINING STORAGE TANK

(75) Inventors: Eugene B. Silverman, Ellicott City, MD (US); Seymour R. Kotler, Annapolis, MD (US); Eric C. Crumption, Severna Park, MD (US)

(73) Assignee: AST Services, LLC., Danbury, CT (US)

( * ) Notice: Subject to any disclaimer, the term of this patent is extended or adjusted under 35 U.S.C. 154(b) by 281 days.

(21) Appl. No.: 10/224,292

(22) Filed: Aug. 20, 2002

(65) Prior Publication Data

US 2004/0036859 A1 Feb. 26, 2004

(51) Int. Cl.$^7$ ............................................. G01N 21/88
(52) U.S. Cl. .................... 356/237.1; 73/864.67
(58) Field of Search ................. 356/241.1–241.6, 356/237.1, 237.2, 237.3; 73/31, 1.22, 623, 864.67; 348/82, 84; 220/216, 218, 221

(56) References Cited

U.S. PATENT DOCUMENTS

| | | | |
|---|---|---|---|
| 5,138,891 A | * | 8/1992 | Johnson .................... 73/864.67 |
| 5,205,174 A | | 4/1993 | Silverman et al. |
| 5,372,270 A | | 12/1994 | Rosenkrantz |
| 5,423,446 A | * | 6/1995 | Johnson ....................... 220/216 |
| 5,565,981 A | * | 10/1996 | Winstead et al. ........ 356/241.1 |
| 5,627,800 A | | 5/1997 | Kotler et al. |
| 5,704,509 A | | 1/1998 | Rosenkrantz |
| 5,956,077 A | * | 9/1999 | Qureshi et al. ................ 348/82 |
| 5,956,135 A | * | 9/1999 | Quesnel .................... 356/241.1 |
| 6,104,970 A | * | 8/2000 | Schmidt et al. ................. 701/2 |

FOREIGN PATENT DOCUMENTS

EP    1 156 304 A1    11/2001

OTHER PUBLICATIONS

SEAMAY DPC–7000 Underwater Digital Photo Camera User Manual (Apr. 2002) Deep Sea Systems International Inc., Cataumet, MA.

* cited by examiner

*Primary Examiner*—Gregory J. Toatley, Jr.
*Assistant Examiner*—Sang H. Nguyen
(74) *Attorney, Agent, or Firm*—David M. Rosenblum

(57) ABSTRACT

Methods for remotely inspecting an internal floating roof and the seals associated with such internal floating roof project an illumination pattern from a series of substantially parallel laser beams onto the floating roof and/or the seal. Another laser beam projects at a predetermined angle offset from the series of laser beams. The illumination pattern and offset spot from the other laser are viewed through a camera. The length of a defect in the internal floating roof or seal or a gap between the seal and the tank wall is calculated as the length of a side of a right triangle based upon the predetermined angle and the predetermined distance between the lasers and the floating roof or seal.

47 Claims, 3 Drawing Sheets

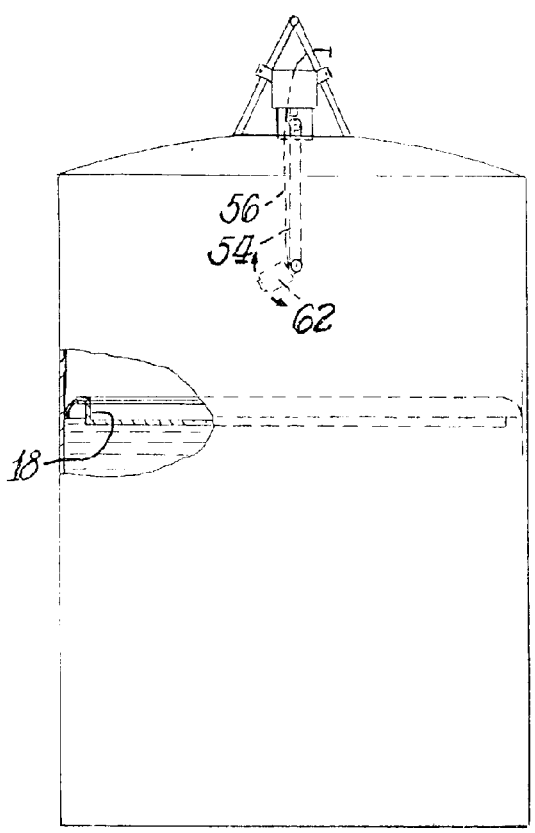
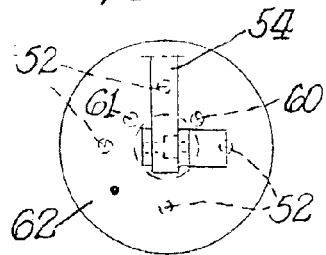
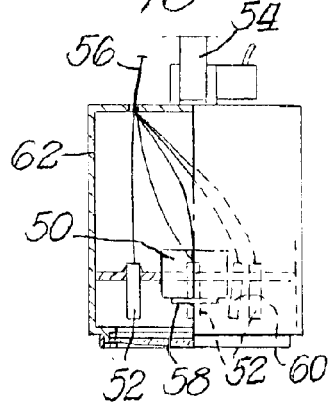
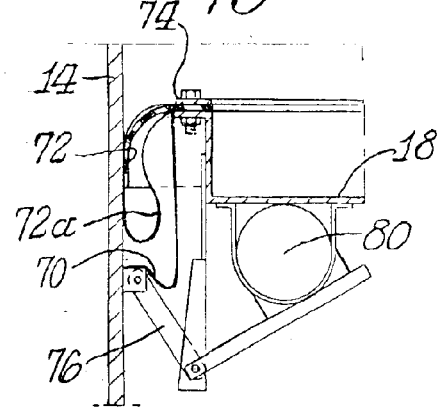
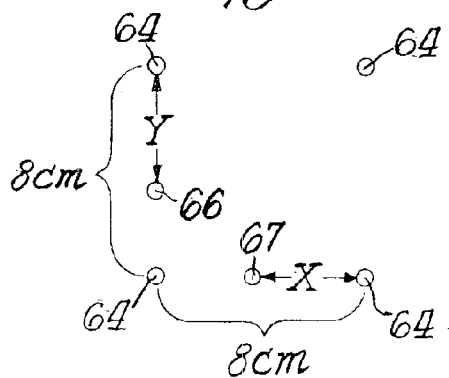

METHOD FOR INSPECTING AN INTERNAL FLOATING ROOF IN A LIQUID-CONTAINING STORAGE TANK

This invention concerns an inspection method for determining the dimensions of a defect or gap in an internal floating roof of a storage tank or in a seal associated with such internal floating roof. The method permits accurate assessment of such defect or gap without requiring a worker to enter the vapor space above the floating roof and without requiring the tank to be drained.

BACKGROUND OF THE INVENTION

An internal floating roof storage tank generally has a solid cylindrical outer wall covered by a solid sloped or dome-shaped roof. An internal floating roof is held within the volume defined by the outer wall and roof. The internal floating roof extends over the liquid contents held within the volume, and forms a vapor seal around the internal circumference of the cylindrical wall. The height within the tank at which the internal floating roof is positioned varies according to the amount of liquid being stored within the tank at any given time.

Internal floating roof storage tanks generally are used to store volatile or flammable liquids, such as gasoline. A vapor space is formed inside the tank, between the internal floating roof covering the gasoline and the outer tank roof. Vapors emitted from the internal volume of the storage tank collect in the volume between the floating roof and the external roof. This volume is vented to the atmosphere. Environmental protection regulations restrict the amount of hydrocarbon vapors that may be released to the atmosphere. Air quality may be impacted adversely if hydrocarbon vapor emissions exceed permitted amounts.

Manual access to the internal volume of the tank is provided within the vapor space. One or more access ports or doorways are formed in the roof or outer wall of the tank, and a ladder or gangway may be supported within the vapor space. Persons may enter the vapor space to service the tank, the internal floating roof and any equipment housed inside the tank. Because of the hazards associated with confined space entry within the vapor space, particularly in flammable atmospheres, entry for inspection purposes is rarely permitted.

UL 913-1988 sets forth the standards that must be satisfied before equipment may be introduced into an internal floating roof storage tank or the vapor space above the floating roof in such tank. "Intrinsically safe" apparatus are protected against ignition by (1) limiting the maximum current and voltage that may be applied so that the energy available in a hazardous location is not capable of igniting the flammable mixture in such location; and (2) taking precautions against spark ignition and thermal ignition that could ignite and create an explosion.

Special precautions are taken when introducing equipment into the internal volume of the internal floating roof storage tank when the tank volume holds a flammable liquid, such as gasoline. Measures are taken to prevent sparks and associated combustion of flammable vapors. Measures are also taken to minimize the amount of time the seal between the flammable liquid and the vapor space above the internal floating roof is broken to prevent substantial amounts of flammable vapors from being emitted into the vapor space.

Internal floating roof storage tanks are inspected at regular intervals to locate cracks, corrosion or other defects that might lead to tank failure. Environmental protection regulations specify the frequency and recommended procedures for inspecting tanks for structural integrity. One method involves introducing a remote controlled submersible vehicle into the tank while the tank remains in service. For example, U.S. Pat. No. 5,205,174 discloses a scavenger submersible vehicle that inspects the internal surfaces of a liquid filled tank using a video camera and/or ultrasound pulses. One or more umbilical hose(s) and wire harness(es) connect the remote-controlled vehicle to its power source and air or vacuum source, and further provide a link for transmitting navigation and inspection data from the vehicle to one or more computers located outside the tank.

Safety and environmental regulations (i.e., 40 CFR 60, subparts K, Ka and Kb) further require that the primary and secondary seals between the periphery of a floating roof and the internal side wall of a tank be inspected at regular intervals. When the tank volume is filled with a hazardous liquid such as a petrochemical like gasoline or other chemical, a cursory visual inspection may be made by a worker who enters the vapor space above the internal floating roof and walks upon the floating roof. Entry into the vapor space poses several dangers, however. First, the vapor space is potentially explosive and extreme care must be taken to prevent heat or sparks that could ignite an explosion. Second, the vapors in the vapor space can be harmful if breathed in.

Remote inspection of the internal floating roof and the primary and secondary seals associated with an internal floating roof storage tank has been accomplished by lowering a camera into the vapor space to photograph regions of the seal. This qualitative method has been used to identify regions that should be visually inspected more closely by a worker as a way to help shorten the time the worker remains in the vapor space.

No method has yet been found to inspect the seal and provide an accurate quantitative assessment of the dimensions of a defect or gap without having a worker enter the vapor space. An accurate remote inspection method continues to be sought.

SUMMARY OF THE INVENTION

A method for inspecting an internal floating roof and seal(s) associated with such internal floating roof in a liquid containing storage tank has advantages over prior methods. In the preferred method a worker does not need to physically enter the vapor space above the floating roof, walk along the floating roof or depend only upon a cursory visual assessment. Rather, to inspect the upper surface of the floating roof and the seal(s) associated therewith, a camera is inserted into the vapor space above the floating roof at a predetermined distance above an upper surface of the floating roof. A series of lasers is also inserted into the vapor space at such predetermined distance above the upper surface of the floating roof.

Preferably, the camera and lasers are suspended from a pole at the distal end of such pole. The proximal end of the pole remains outside of the vapor space. It may be held by a worker or a held by a tripod or jig or other holding equipment. Most preferably, the laser sources are positioned around the camera lens in a regular array, such as four lasers in a polygonal (e.g., square) array with each beam forming a corner of such array.

The first plurality of laser beams are parallel or substantially parallel to one another. The beams project onto an upper surface of the floating roof or onto a seal associated with the upper surface of the floating roof. Where the beams form a series in a regular pattern—such as a square, the illumination pattern formed on the upper surface or seal is a square with a laser spot beam at each corner.

Another laser beam projects at an angle offset from the angle at which the first plurality of laser beams project. Preferably, this other laser beam is offset by 1° to 3° from the angle at which the plurality of beams project. The offset angle causes this other laser beam to illuminate a spot generally spaced apart from the illumination pattern from the plurality of lasers. The distance the spot is spaced apart depends upon the predetermined distance between the lasers and the upper surface or seal region being inspected and the offset angle. This distance can be precisely calculated using trigonometry where the distance or length comprises one side of a right triangle, where the other side comprises the predetermined distance, and the acute angle opposite the one side is the offset angle.

The illumination pattern formed by the laser plurality and the spot formed by the other laser are viewed through the camera. The illumination pattern is projected onto the upper surface of the floating roof to inspect defects in such surface. Alternatively, the illumination pattern is projected onto a seal surface near to a defect in the seal or near to a gap between the seal and the tank wall. The dimensions of the defect or the gap are assessed based on the known distance between each laser in the plurality array, and by calculating the distance between the spot and the illumination pattern. The camera and lasers are moved to project the illumination pattern and spot onto different portions of the upper surface of the floating roof or of the seal and the tank wall in order to inspect those different portions.

Preferably, the lasers forming the illumination pattern, such as the square grid, are one color, e.g., green, and the other laser is a different color, e.g., red. However, lasers of the same color may be used with good results.

In a particularly preferred embodiment, the plurality of lasers forms an illumination pattern that is a square grid, with a spot from each laser forming one corner of the grid, and the other laser is positioned along a side of the square between two of the lasers in the plurality. In this particularly preferred embodiment, a sixth laser is positioned along a different, but adjacent, side of the square between two of the lasers in the plurality. The another laser and the sixth laser project at angles offset from the angle of projection of the lasers in the plurality of lasers.

To inspect the underside or lower surface of the internal floating roof and the primary seal associated therewith, the camera may be lowered through the vapor space above the internal floating roof, through a hatchway in the internal floating roof and into the liquid contents held within the liquid storing volume of the internal floating roof storage tank. The camera lens is directed toward the underside of the internal floating roof and primary seal to visually inspect the surfaces of the internal floating roof and/or primary seal for defects or gaps. As noted above, a series of laser sources also may project a laser beam illumination pattern onto the surfaces to determine the dimensions of any defects or gaps found on the surfaces. The laser sources may be mounted within the camera housing or may be separately mounted. While the camera and laser sources may be attached to the distal end of a pole or boom, preferably, they are associated with a robotic inspection vehicle deployed within the tank. In such preferred embodiment, the camera tilts from a first position directed toward the floor and/or sidewalls of the liquid filled storage tank to a second position directed toward the underside of the internal floating roof and/or the primary seal associated with such roof. Such tilting camera may include laser sources integrally mounted into the camera housing.

DESCRIPTION OF THE DRAWINGS

FIG. 2 is a side elevational view of an internal floating roof storage tank with a seal inspection camera deployed therein;

FIG. 3 is a partial view in side elevation of an internal floating roof with a seal at its internal periphery;

FIG. 4 is a side elevational view partially broken away showing the inspection camera with lasers in a sealed housing attached to a pole end;

FIG. 5 is top plan view of FIG. 4 showing the camera with a series of four laser sources disposed in a square array and a fifth laser source disposed along one side of said array and a sixth laser source disposed along another side of said array;

FIG. 6 is a laser pattern projected onto an internal wall surface of the internal floating roof storage tank;

DESCRIPTION OF THE PREFERRED EMBODIMENTS

Figure 1:
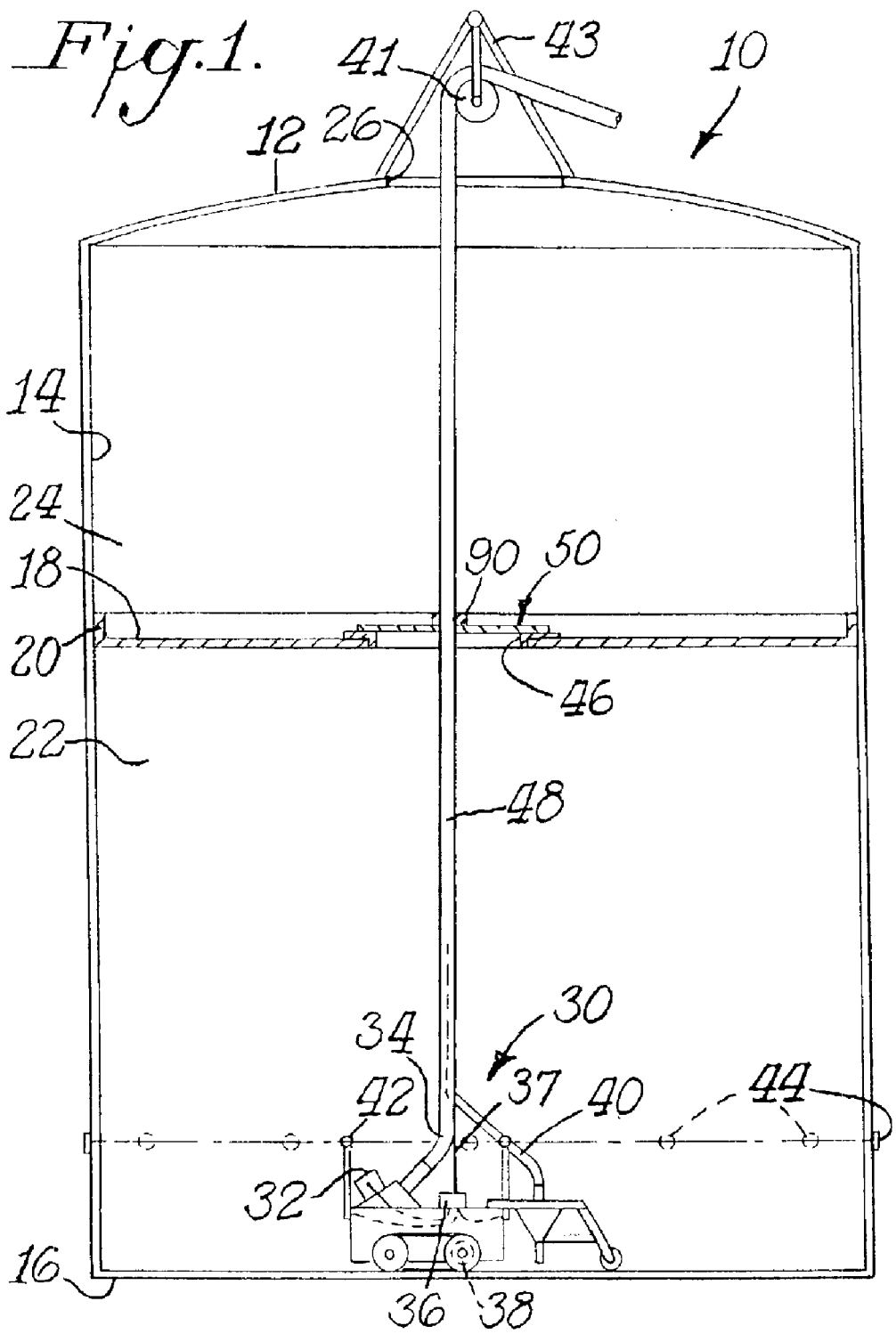
FIG. 1 is a side elevational view of an internal floating roof storage tank with an inspection vehicle deployed therein.

Referring first to FIG. 1, a floating roof storage tank 10 has a sloped or dome-shaped roof 12 over a cylindrical side wall 14 and a floor 16. The floating roof storage tank 10 includes a floating roof 18 separating the liquid 22 within the liquid holding volume from the vapor space 24 above the liquid holding volume. The floating roofs most frequently are formed from aluminum. A vapor seal 20 is formed at the edges of the floating roof 18 and contacts the internal wall of the side wall 14 to limit or prevent vapors from a volatile liquid stored in the tank from escaping the liquid holding volume under the floating roof 18.

For the tank shown in FIG. 1, a manway access port 26 through the roof 12 provides access to the vapor space 24 above the floating roof 18 for inspection and maintenance personnel. The tank may include one or a series of ladders (not shown) adjacent the internal side wall 14 of the tank leading from the access port 26 to the upper surface of the floating roof 18.

As shown in FIG. 1, an inspection vehicle 30 has been introduced into the liquid holding volume within the floating roof tank 10. The vehicle 30 traverses along the internal surface of the floor 16 to inspect the floor 16 for cracks or corrosion that could lead to tank failure. The vehicle 30 is equipped with a camera 32 to transmit video signals to a computer (not shown) located outside the tank 10. The vehicle 30 is hydraulic motor 38 controlled and is provided with an electronic control module 36 that is linked via electric cable within an umbilical connection 37 to a power source (not shown) located outside the tank 10. The vehicle 30 is also equipped with sensors (sonic transducers) 42 that communicate with transducers 44 mounted in an array on the outer surface of the side wall 14 of the tank 10. The sensors 42 and transducers 44 transmit and/or receive signals, and the data from the sensors is transmitted to a computer (not shown) located outside the tank, which computer analyzes such data to determine the position of the vehicle within the tank 10. The vehicle 30 is also provided with a blower and blower line 40 and a vacuum or suction line 34 that work independently or in combination to clear away debris from the internal surface of the floor 16 prior to inspecting that surface. Additional details about inspection vehicles and the means for operating and navigating such vehicles are shown in U.S. Pat. Nos. 5,205,174 and 5,627,800, the disclosures of which are incorporated herein by reference.

Hydraulic tubing forming a suction line 34 in combination with a blower line 40 is joined with one or more cables for transmitting electric signals to the vehicle and transmitting electric signals back to the computer. The tubing and blower line and cable(s) together form an umbilical cord 48 that is installed over a pulley 41. As shown in FIG. 1, the pulley 41 is mounted to a tripod 43 installed over the outer roof 12. The umbilical cord 48 has sufficient strength to hold the vehicle 30 as it is lowered into the liquid holding volume inside the tank 10 and when it is lifted out of the liquid holding volume inside the tank 10.

A hatchway 46 is provided through the floating roof 18. The vehicle 30 preferably has a height and width that allow the vehicle to be passed through the hatchway 46 when the existing hatch cover provided on the floating roof 18 has been removed. It is also possible to install a second tripod with a pulley (not shown) on the floating roof 18 and over the hatchway 46 where the internal floating roof has sufficient stability to support such weight.

An internal floating roof is sealed at its periphery to limit or prevent hazardous vapors from escaping the tank and flowing into the vapor space above the floating roof. Referring to FIG. 3, the floating roof 18 generally is sealed with a combination of a primary seal 70 and a secondary seal 72. The floating roof rests on an air bladder or pontoon 80 that floats on the liquid surface of the liquid stored in the tank. The primary seal 70 comprises a series of flanges hinged together at one end with the other end of such flanges linked to the pontoon, floating roof or inner peripheral side wall respectively. A vapor barrier fabric 76 has one end connected to the floating roof and the other end connected to the upper portion of a shoe section or bracket attached to the inner peripheral side wall of the tank. The secondary seal 72 comprises a polymeric material formed into a peripheral ring that is linked to the periphery of the internal floating roof with a series of brackets 74. The secondary seal 72 overlays the primary seal 70. The secondary seal 72 frictionally contacts the internal tank side wall 14 surface forming a vapor barrier. The secondary seal 72 also in part supports the internal floating roof 18 over the liquid stored in the tank.

The primary 70 and secondary 72 seals shown in FIG. 3 represent one such type of seal shown for purposes of illustration. See also U.S. Pat. No. 5,372,270 for further details on this type of floating roof construction. Various alternative floating roof and seal constructions are known, and the invention claimed herein is not limited to use with any one type of floating roof or floating roof seal.

Gaps between the outer peripheral edge of the secondary seal 72 and the tank side wall 14 can indicate a seal failure or a condition that would lead to a seal failure. Tanks and the internal floating roof primary and secondary seals thus are regularly inspected to assess and prevent hazardous conditions that could lead to failure.

Referring next to FIG. 2 and FIG. 4, a camera housing 62 that is mounted to or suspended from the distal end of a pole or boom 54 is inserted into the vapor space above the internal floating roof tank 10. The proximal end of the pole 54 remains outside the tank, and is supported on a harness attached to a tripod. Power cables and transmissions cables 56 link the camera 50 to a remote control station outside the tank (not shown). The camera 50 preferably transmits video images from its lens 58 to a remote processor and monitor (not shown).

The camera 50 is shown in FIG. 4 and FIG. 5. A series of lasers 52 are mounted within the camera housing 62 in a regular square grid. Preferably, the lasers 52 form the corners of the square, with each laser spaced 80 mm from each adjacent laser. The laser beams are aligned substantially parallel and straight. Lasers project laser beams through fluids, including optically clear liquids and gases. Laser beams do not distort or bend when projected through the vapor in a vapor space over an internal floating roof tank.

Figure 8:
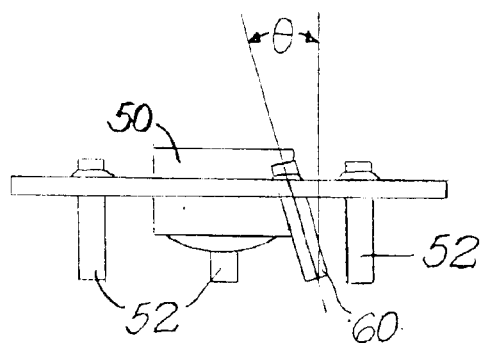
FIG. 8 is a front elevational view showing the inspection camera lens and lasers.

Referring to FIGS. 4, 5 and 8, a fifth laser 60 is mounted on the camera housing along a first side of the grid. This fifth or additional laser 60 is oriented such that it projects a laser beam offset at an angle different from the laser beams from lasers 52. Preferably the fifth laser 60 is offset to project at an angle $\theta$ in the range from about +1° to about +3° (or about −1° to about −3°) from an axis parallel to axis of projection of the lasers 52 in the regular grid.

Figure 9:
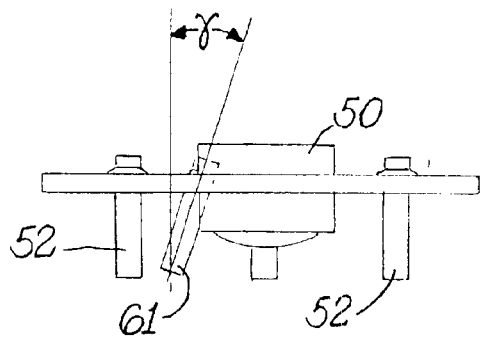
FIG. 9 is a left side elevational view showing the inspection cameral lens and lasers.

Referring to FIGS. 4, 5 and 9, a sixth laser 61 is mounted on the camera housing along a second side of the grid. This sixth or other additional laser 61 is oriented such that it projects a laser beam offset at an angle different from the laser beams from lasers 52. Preferably, the sixth laser 61 is offset to project at an angle $\lambda$ in the range from about +1° to about +3° (or about −1° to about −3°) from an axis parallel to axis of projection of the lasers 52 in the regular grid.

While an integrated camera with laser rangefinders is preferred, alternate arrangements in which a camera is separate from a series of lasers may also be used. If an integrated camera and laser rangefinder is selected, a preferred camera is the QCAM IT1-S digital underwater camera manufactured by Tritech International Limited of Aberdeen, Scotland, UK. An alternative camera is the SeaMax DPC-7000 underwater digital camera from Deep Sea Systems International, Inc. of Cataumet, Mass. The camera and laser sources and the power transmission and image transmission cabling preferably are designed as intrinsically safe so as to permit the entry into the vapor space and hazardous liquid-containing volume of an internal floating roof storage tank without risk of sparks or ignition or explosion.

As shown in FIG. 6, the lasers 52 project an illumination pattern of a series of spots 64 in a square grid with each spot 64 separated from an adjacent spot by 80 mm (preferred embodiment). Alternate spot spacing and alternate regular grid patterns of course could be used with the method of the invention. If the laser sources are directed toward a target such that the laser beams are perpendicular to that target, the resulting illumination pattern will have the regular square grid as shown in FIG. 6, with each spot 64 separated by 80 mm. When the laser sources are projected onto the target at an angle, the distance of separation between two of the spots 64 may be different for two of the parallel sides, but may remain 80 mm between the other two parallel sides, such that the illumination pattern of spots 64 forms a rectangle rather than a square.

The fifth laser 60 projects a spot 66 that is spaced apart from one of the spots 64 by a distance X (FIG. 6). The sixth laser 61 projects a spot 67 that is spaced apart from one of the other spots 64 by a distance Y (FIG. 6). The distances X and Y may be calculated by simple trigonometry. In the preferred embodiment, a software algorithm is supplied with the controls for the camera. With this algorithm, it is possible to calculate the distance between the camera and the target upon which the illumination pattern is formed, as well as the distances X and Y, based upon predetermined parameters: (i) the angles θ and λ, which may be the same or different, and (ii) the separation between the lasers 52, and (iii) the separation between the lasers 52 and lasers 60 and 61, respectively; and based upon measured parameters: the spacing of the spots 64 in the illumination pattern. If the illumination pattern forms a rectangle by connecting the spots 64 formed at the corners, the distance for measurement (X or Y) is selected as the spot 66 (for X) or 67 (for Y) formed along the side between spots 64 that measures 80 mm. If both sides along which spots 66 and 67 are formed correspond to 80 mm, the camera and laser sources are projected perpendicularly toward the target, and determinations of both X and Y can be made with reasonable accuracy.

The lasers and camera are lowered into the vapor space at a predetermined distance from the upper surface of the floating roof and from other surfaces defining that vapor space. The distance X comprises the length of one side of a right triangle that is opposite the acute angle of the offset angle θ. The other side of the triangle comprises the predetermined distance between the lasers and the surface onto which the illumination pattern is formed. The distance Y comprises the length of one side of a right triangle that is opposite the acute angle of the offset angle λ. The other side of the triangle comprises the predetermined distance between the lasers and the surface onto which the illumination pattern is formed.

Figure 7:
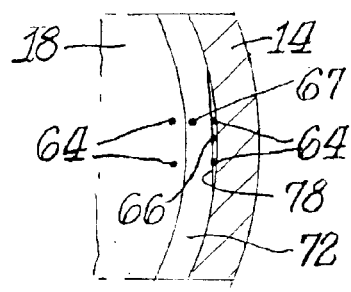
FIG. 7 is a partial top plan view of the internal floating roof tank with a seal at the internal periphery of the tank as shown in FIG. 3 showing more particularly a gap between the seal and the internal periphery of the tank and a laser pattern projected onto an upper surface of the seal.

As shown in FIG. 7, a gap 78 between the peripheral edge of the secondary seal 72 and the side of the tank wall can be determined using the method of the invention. The lasers 52 are projected to form an illumination pattern 64 on the seal 72. The fifth laser 60 offset from the plurality of lasers 52 projects to form a spot 66 between two of the spots 64 in the illumination pattern. The sixth laser 61 offset from the plurality of lasers 52 projects to form a spot 67 between two of the spots 64 in the illumination pattern. The laser sources and camera positions are adjusted to project the illumination pattern and offset spots 66 and/or 67 over a gap. The dimension (length or width) of the gap is calculated based on the known trigonometric relationships between the regular grid of the illumination pattern and the offset spot(s).

Safety regulations require that the primary and secondary seals contact the internal side wall of a floating roof tank to prevent substantial vapors from escaping into the vapor space above the internal floating roof. If a gap is present between a secondary seal and the tank wall, federal regulations (40 CFR 60.113b) require the gap not exceed 1.27 cm and that the accumulated area of all gaps between the tank wall and the seal not exceed 21.2 $cm^2$ per meter of tank diameter. If a gap is present between a primary seal and the tank wall, federal regulations (40 CFR 60.113b) require the gap not exceed 3.81 cm and that the accumulated area of all gaps between the tank wall and the primary seal not exceed 212 $cm^2$ per meter of tank diameter. The inspection method herein can be used to inspect a seal and determine if gaps are within regulation limits.

Figure 10:
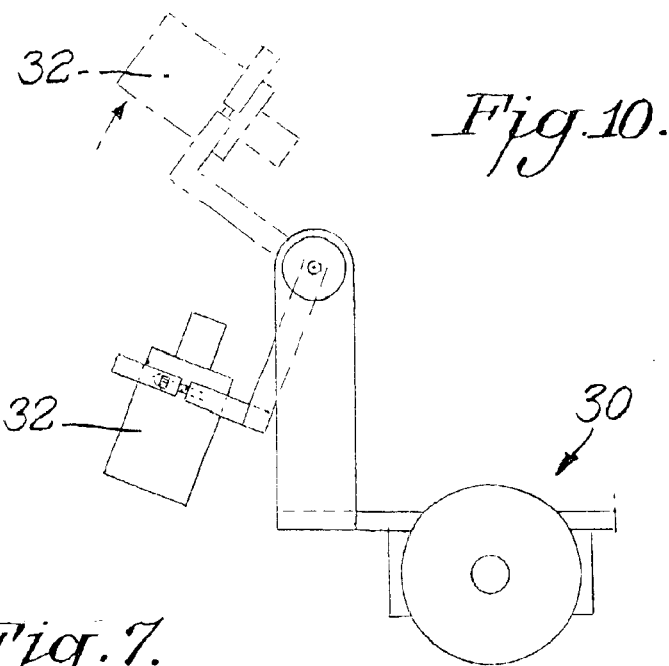
FIG. 10 is a side elevational view of a camera mounted on a pivot bar attached to the inspection vehicle of FIG. 1.

Referring to FIG. 10, the vehicle 30 has a camera 32 and optionally an associated spot light (not shown) that are mounted on a tilting assembly pivoting about a rod held by brackets attached to the vehicle. The camera 32 and spot light may together be turned to focus upwardly onto the tank sidewalls and the underside of the floating roof. The camera 32 enables qualitative visual assessments of the condition of the primary seal 70 between the tank sidewall and internal floating roof. In a particularly preferred embodiment, the camera 32 has associated laser sources mounted directly into the camera housing so that the dimensions of any defect in the underside of the internal floating roof or any gap between the tank sidewall and the primary seal 70 may be calculated using the method described in more detail above.

Alternatively, separate from the camera 32 mounted on the vehicle 30 shown in FIG. 10, the camera 50 mounted on the boom 54 from FIG. 2 may be inserted through a hatchway 46 in the floating roof 18 and directed toward the underside surfaces of the internal floating roof and the primary seal 70 to inspect those surfaces and the seal.

While the invention has particular advantages for determining the dimensions of gaps between the tank side wall and the primary seal 70 and secondary seal 72, other defects in the primary seal 70 and secondary seal 72 also may be assessed both qualitatively and quantitatively using the methods according to the invention.

The invention has been illustrated by detailed description and examples of the preferred embodiments. Various changes in form and detail will be within the skill of persons skilled in the art. Therefore, the invention must be measured by the claims and not by the description of the examples or the preferred embodiments.

We claim:

1. A method for inspecting an internal floating roof in a liquid-containing storage tank, comprising:
   (a) inserting a camera into a vapor space above the floating roof at a predetermined distance above an upper surface of the floating roof or a seal associated therewith;
   (b) projecting a plurality of substantially parallel laser beams onto the upper surface of the floating roof or seal;
   (c) projecting another laser beam at an angle different from the substantially parallel laser beams;
   (d) viewing an illumination pattern formed by the laser beams on the surface;
   (e) calculating a length between the pattern formed by the laser beams and a spot illuminated on the surface by the another laser beam, wherein said length relates to a size of a defect in the floating roof or seal or a distance of separation between the floating roof or seal and the wall surface of the storage tank.

2. The method of claim 1, wherein the laser beams project at an angle y and the another laser beam projects at an angle θ in the range of (y−3°) to (y−1°).

3. The method of claim 1, wherein the laser beams project at an angle y and the another laser beam projects at an angle θ in the range of (y+1°) to (y+3°).

4. The method of claim 1, wherein the camera is suspended from a pole, and wherein the camera is attached at a distal end of the pole and a proximal end of the pole remains outside the vapor space.

5. The method of claim 1, wherein the plurality of laser beams comprises four laser beams that project to form as the illumination pattern the four corners of a rectangle or square or other four-sided polygon.

6. The method of claim 5, further comprising positioning the another laser beam in line with and between two of the four laser beams.

7. The method of claim 5, further comprising positioning a sixth laser beam in line with and between two of the four laser beams.

8. The method of claim 1, wherein the illumination pattern is viewed through a lens of the camera.

9. The method of claim 1, wherein the camera sends an image of the illumination pattern to a viewing location outside of the storage tank.

10. The method of claim 1, further comprising (f) deploying lasers in the camera and positioning the camera so that the laser beams project on the upper surface and the another laser beam projects on the wall surface.

11. The method of claim 1, further comprising (f) deploying lasers in the camera and positioning the camera so that the laser beams project on the wall surface and the another laser beam projects on the upper surface.

12. The method of claim 1, wherein the laser beams are one color and the another laser beam is a different color.

13. The method of claim 7, wherein the laser beams are one color and the another laser beam and the sixth laser beam are a different color.

14. The method of claim 1, wherein the length is calculated as a length of one side of a right triangle formed with a first adjacent side comprising the predetermined distance and an opposite acute angle comprising the different angle at which the another laser beam is projected.

15. A method for inspecting a gap between a seal of an internal floating roof in a liquid-containing storage tank and a tank side wall, comprising:
(a) inserting a camera into a vapor space above the floating roof at a predetermined distance above an upper surface of the floating roof;
(b) projecting a plurality of substantially parallel laser beams onto the seal associated with the upper surface of the floating roof;
(c) projecting another laser beam at an angle different from the substantially parallel laser beams;
(d) viewing an illumination pattern formed by at least a portion of the laser beams on the seal;
(e) calculating a length between the pattern formed by the laser beams and a spot illuminated on the seal or on a wall surface of the storage tank by the another laser beam, wherein said length relates to a distance of separation between the seal and the tank side wall.

16. The method of claim 15, wherein the laser beams project at an angle y and the another laser beam projects at an angle θ in the range of (y−3°) to (y−1°).

17. The method of claim 15, wherein the laser beams project at an angle y and the another laser beam projects at an angle θ in the range of (y+1°) to (y+3°).

18. The method of claim 15, wherein the camera is suspended from a pole, and wherein the camera is attached at a distal end of the pole and a proximal end of the pole remains outside the vapor space.

19. The method of claim 15, wherein the plurality of laser beams comprises four laser beams that project to form as the illumination pattern the four corners of a rectangle or square or other four-sided polygon.

20. The method of claim 19, further comprising positioning the another laser beam in line with and between two of the four laser beams.

21. The method of claim 19, further comprising positioning a sixth laser beam in line with and between two of the four laser beams.

22. The method of claim 21, wherein the laser beams are one color and the another laser beam and the sixth laser beam are a different color.

23. The method of claim 15, wherein the illumination pattern is viewed through a lens of the camera.

24. The method of claim 15, wherein the camera sends an image of the illumination pattern to a viewing location outside of the storage tank.

25. The method of claim 15, further comprising (f) deploying lasers in the camera and positioning the camera so that the laser beams project on the upper surface and the another laser beam projects on the wall surface.

26. The method of claim 15, wherein the laser beams are one color and the another laser beam is a different color.

27. The method of claim 15, further comprising (f) deploying lasers in the camera and positioning the camera so that the laser beams project on the wall surface and the another laser beam projects on the upper surface.

28. The method of claim 15, wherein the length is calculated as a length of one side of a right triangle formed with a first adjacent side comprising the predetermined distance and an opposite acute angle comprising the different angle at which the another laser beam is projected.

29. A method for inspecting an internal floating roof in a liquid-containing storage tank, comprising:
(a) inserting a camera into a liquid-containing volume of the liquid-containing storage tank at a predetermined distance;
(b) directing the camera toward an underside surface of the floating roof or a seal associated therewith;
(c) projecting a plurality of substantially parallel laser beams onto the underside surface of the floating roof or the seal;
(d) projecting another laser beam at an angle different from the substantially parallel laser beams;
(e) viewing an illumination pattern formed by the laser beams on the surface;
(f) calculating a length between the pattern formed by the laser beams and a spot illuminated on the surface by the another laser beam, wherein said length relates to a size of a defect in the floating roof or seal or a distance of separation between the seal or the floating roof and the wall surface of the storage tank.

30. The method of claim 29, wherein the laser beams project at an angle y and the another laser beam projects at an angle θ in the range of (y−3°) to (y−1°).

31. The method of claim 29, wherein the laser beams project at an angle y and the another laser beam projects at an angle θ in the range of (y+1°) to (y+3°).

32. The method of claim 29, wherein the camera is suspended from a pole, and wherein the camera is attached at a distal end of the pole and a proximal end of the pole remains outside the liquid-containing volume.

33. The method of claim 29, wherein the plurality of laser beams comprises four laser beams that project to form as the illumination pattern the four corners of a rectangle or square or other four-sided polygon.

34. The method of claim 33, further comprising positioning the another laser beam in line with and between two of the four laser beams.

35. The method of claim 33, further comprising positioning a sixth laser beam in line with and between two of the four laser beams.

36. The method of claim 35, wherein the laser beams are one color and the another laser beam and the sixth laser beam are a different color.

37. The method of claim 29, wherein the illumination pattern is viewed through a lens of the camera.

38. The method of claim 29, wherein the camera sends an image of the illumination pattern to a viewing location outside of the storage tank.

39. The method of claim 29, further comprising (f) deploying lasers in the camera and positioning the camera so that the laser beams project on the underside surface and the another laser beam projects on the wall surface.

40. The method of claim 29 wherein the laser beams are one color and the another laser beam is a different color.

41. The method of claim 29, further comprising (f) deploying lasers in the camera and positioning the camera so that the laser beams project on the wall surface and the another laser beam projects on the underside surface.

42. The method of claim 29, wherein the length is calculated as a length of one side of a right triangle formed with a first adjacent side comprising the predetermined distance and an opposite acute angle comprising the different angle at which the another laser beam is projected.

43. The method of claim 29, wherein the camera is mounted to an inspection vehicle deployed within the tank.

44. A method for inspecting an internal floating roof or a seal associated therewith in a liquid-containing storage tank, comprising:

(a) inserting a camera into a liquid-containing volume of the liquid-containing storage tank wherein said camera is mounted for tiltable movement onto an inspection vehicle;

(b) directing the camera toward a target on the underside surface of the floating roof or the seal; and (c) electronically transmitting a visual image of the target for processing or analyzing outside of the liquid-containing volume.

45. The method of claim 44, further comprising one or more light sources mounted for tiltable movement onto the inspection vehicle.

46. The method of claim 44, wherein the camera is tiltable from a first position for inspecting a floor surface of the storage tank to a second position directed toward the target.

47. The method of claim 45, wherein the light source(s) are tiltable from a first position for inspecting a floor surface of the storage tank to a second position directed toward the target.

* * * * *